US010381795B2

(12) United States Patent
Kim

(10) Patent No.: US 10,381,795 B2
(45) Date of Patent: Aug. 13, 2019

(54) UNIDIRECTIONALLY EMITTING MICRODISK HAVING ULTRA-HIGH QUALITY FACTOR AND LASER USING THE SAME

(71) Applicant: Daegu Gyeongbuk Institute of Science and Technology, Daegu (KR)

(72) Inventor: Chil Min Kim, Seoul (KR)

(73) Assignee: Daegu Gyeongbuk Institute of Science and Technology, Daegu (KR)

(*) Notice: Subject to any disclaimer, the term of this patent is extended or adjusted under 35 U.S.C. 154(b) by 0 days.

(21) Appl. No.: 15/690,725

(22) Filed: Aug. 30, 2017

(65) Prior Publication Data

US 2018/0159295 A1    Jun. 7, 2018

Related U.S. Application Data

(63) Continuation of application No. PCT/KR2016/011206, filed on Oct. 6, 2016.

(30) Foreign Application Priority Data

Oct. 22, 2015  (KR) ........................ 10-2015-0147524

(51) Int. Cl.
| | | |
|---|---|---|
| *H01S 5/10* | (2006.01) | |
| *H01S 3/081* | (2006.01) | |
| *G01N 21/70* | (2006.01) | |
| *H01S 3/063* | (2006.01) | |
| *H01S 3/083* | (2006.01) | |
| *H01S 5/04* | (2006.01) | |

(Continued)

(52) U.S. Cl.
CPC ........... *H01S 3/0818* (2013.01); *G01N 21/70* (2013.01); *H01S 3/063* (2013.01); *H01S 3/083* (2013.01); *H01S 3/0816* (2013.01); *H01S 5/041* (2013.01); *H01S 5/1075* (2013.01); *G01N 21/7746* (2013.01); *H01S 3/091* (2013.01); *H01S 5/32333* (2013.01)

(58) Field of Classification Search
CPC ..... H01S 5/1042; H01S 5/1075; H01S 3/0632
See application file for complete search history.

(56) References Cited

U.S. PATENT DOCUMENTS

| | | | |
|---|---|---|---|
| 7,319,710 B2* | 1/2008 | Kim | H01S 3/0604 372/66 |
| 2002/0018611 A1 | 2/2002 | Maleki et al. | |
| 2004/0218654 A1* | 11/2004 | Kneissl | B82Y 20/00 372/94 |

FOREIGN PATENT DOCUMENTS

| | | |
|---|---|---|
| KR | 1020020028432 | 4/2002 |
| KR | 1020060001735 | 1/2006 |

(Continued)

OTHER PUBLICATIONS

Lee, "Unidirectional resonance modes supported by secondary islands in a microcavity comprised of two half ellipses," Mar. 15, 2011, Phys Rev A, 80, pp. 033815-1-033815-4.*

(Continued)

*Primary Examiner* — Michael Carter
(74) *Attorney, Agent, or Firm* — Myers Bigel, P.A.

(57) ABSTRACT

The present invention relates to a microdisk laser having characteristics of unidirectional emission and an ultra-high quality factor and also a microdisk laser composed of four circular arcs and configured to emit light in one direction in a resonance mode having the form of a whispering gallery mode formed by total reflection.

16 Claims, 8 Drawing Sheets

(51) Int. Cl.
*H01S 3/091* (2006.01)
*G01N 21/77* (2006.01)
*H01S 5/323* (2006.01)

(56) References Cited

FOREIGN PATENT DOCUMENTS

| | | |
|---|---|---|
| KR | 1020060001739 | 1/2006 |
| WO | 2012154209 | 11/2012 |

OTHER PUBLICATIONS

Weirsig, "Combining Directional Light Output and Ultralow Loss in Deformed Microdisks," Jan. 25, 2008, Phys. Rev. Lett., 100, pp. 033901-1-033901-4.*
Kurdoglyan, "Unidirectional lasing from a microcavity with a rounded isosceles triangle shape," Dec. 1, 2004, Optics Letters, vol. 29, No. 23, pp. 2758-2760. (Year: 2004).*
International Search Report and Written Opinion for PCT/KR2016/011206 dated Dec. 14, 2016, 10 pages (no translation).

\* cited by examiner

UNIDIRECTIONALLY EMITTING MICRODISK HAVING ULTRA-HIGH QUALITY FACTOR AND LASER USING THE SAME

TECHNICAL FIELD

The present invention relates to a microdisk having characteristics of unidirectional emission and ultra-high quality factor and a laser using the same, and more particularly, to a microdisk that has an ultra-high quality factor and is capable of unidirectional emission by a shape composed of four arcs and a laser using the same.

BACKGROUND ART

In optical technology, recently, active research for developing high-precision sensors capable of measuring biomolecules, nanoparticles, deuterium ratios, etc. has been studied by means of an ultra-high quality factor resonator. For such applications, a circular resonator has been used, where a whispering gallery mode is formed inside the circular resonator by introducing an external light source into the circular resonator. Then, when a biomolecule or a nanoparticle is adhered to the surface of the circular resonator, the wavelength is shifted in a resonance mode. Development has been conducted on techniques for measuring such a shift to detect a biomolecule or a nanoparticle. In this case, a quality factor (i.e., Q factor) needs to be extremely high in order to measure a very small variation of the wavelength formed by the adhesion of the biomolecule or nanoparticle. Since such an ultra-high quality factor resonator is implemented by only a circular resonator, development of sensors has been focused on a circular resonator.

However, since a circular resonator emits light in all directions and needs to couple with an external light source, an optical fiber has to be closely coupled with the resonator so that the emitted light can be delivered through the optical fiber. However, in this coupling, there is a drawback, that is, when the position of the optical fiber is slightly changed, the quality factor of the resonator decreases or the optical fiber does not well couple with the resonator. Also, in such a shape, measurement is not properly achieved when the optical fiber is perturbed even by small external vibration. Therefore, a sensor using a circular resonator has a great problem in commercialization due to these problems.

A resonator capable of solving the problems is a unidirectionally emitting microdisk laser. As unidirectionally emitting microdisk lasers, a spiral shape, a rounded triangular shape, a Limagon shape, an ellipse with a notch shape, a half-circular and half-elliptic shape have been proposed up to now.

However, the unidirectionally emitting microdisk lasers that have been developed up to now are highly unidirectional but their quality factors are low, and thus the unidirectionally emitting microdisk lasers that have been developed up to now have still many challenges to be overcome for commercialization. A circular resonator has a quality factor of up to $10^9$, but deformed resonators capable of unidirectional emission has a quality factor of less than $10^6$. When an ultra-high quality factor microdisk resonator that emits unidirectional light is achieved, the ultra-high quality factor microdisk resonator can unidirectionally emit light while maintaining a high quality factor. Accordingly, it is possible to develop the ultra-high quality factor microdisk resonator as an ideal sensor.

DETAILED DESCRIPTION OF THE INVENTION

Technical Problem

The present invention is directed to providing a microdisk having an ultra-high quality factor and having characteristics of unidirectional emission in which laser light having directionality is emitted, due to four circular arcs.

The present invention is also directed to providing a microdisk laser using such a microdisk.

Technical Solution

In order to achieve the described purpose, a microdisk for forming an ultra-high quality factor resonance mode in a chaotic resonator is provided according to an embodiment of the present invention. The microdisk has a first arc having a first radius R1; third and fourth arcs tangentially connected to both ends of the first arc; and a second arc having a second radius R2 greater than the first radius R1 and tangentially connected to the third and fourth arcs.

The ultra-high quality factor resonance mode may be a resonance mode of the resonator formed in the form of a whispering gallery mode in the chaotic resonator.

The ultra-high quality factor resonance mode may be a resonance mode that is localized on a stable periodic orbit positioned at an edge of the chaotic resonator or an unstable periodic orbit positioned at an edge of the chaotic resonator.

The ultra-high quality factor resonance mode may be a resonance mode that is localized on a marginally unstable periodic orbit positioned at an edge of the chaotic resonator or an unstable periodic orbit positioned around the boundary of the chaotic resonator.

According to an embodiment, the microdisk may have emission intensity greater in one direction than in other directions. Preferably, the microdisk laser may unidirectionally emit light.

Also, when the third arc has a third radius R3 and the fourth arc has a fourth radius R4, the third radius and the fourth radius may be smaller than the first radius.

The first, second, third, and fourth arcs may each be formed as a circular arc or a portion of an ellipse.

According to an embodiment, the fourth radius R4 and the third radius R3 may be formed smaller than or equal to $1-10^{-7}$ times the first radius R1. Also, the fourth radius R4 and the third radius R3 may each be in the range between 5% and 99.99999% of the first radius R1.

According to an embodiment, the second radius R2 may be formed greater than or equal to $1+10^{-7}$ times the first radius R1. Also, the second radius R2 may be infinite so that the second arc becomes a straight line.

Points at which the first arc meets the third and fourth arcs and points at which the third and fourth arcs meet the second arc may each be a point at which the two corresponding arcs are tangentially connected to have the same first order derivative value.

Also, points at which the first arc meets the third and fourth arcs and points at which the third and fourth arcs meet the second arc may each be a point at which a difference in first order derivative value is 10% or less.

According to an embodiment, when the third arc has a third radius R3 and the fourth arc has a fourth radius R4, the third radius R3 may be equal to the fourth radius R4.

In order to achieve the described purpose, a microdisk laser according to another embodiment of the present invention is provided. The microdisk laser includes a power supply unit; a microdisk having a first arc having a first radius R1, third and fourth arcs tangentially connected to both ends of the first arc, and a second arc having a second radius R2 greater than the first radius R1 and tangentially connected to the third and fourth arcs; and an electrode formed by coating an upper surface of the microdisk with metal and configured to supply electric current.

According to an embodiment, in order to generate a whispering gallery mode, the microdisk may supply power along a path, where a whispering gallery mode is localized.

In order to achieve the described purpose, a configuration of a microdisk laser according to still another embodiment of the present invention is provided. The microdisk laser includes a microdisk having a first arc having a first radius R1, third and fourth arcs tangentially connected to both ends of the first arc, and a second arc having a second radius R2 greater than the first radius R1 and tangentially connected to the third and fourth arcs; and a light supply unit configured to supply light to the microdisk to excite the microdisk.

According to an embodiment, in order to generate a whispering gallery mode, the light supply unit may supply light along an edge of the microdisk to excite the microdisk.

Advantageous Effects of the Invention

With the microdisk and the laser using the same according to the present invention, the microdisk has an ultra-high quality factor because the microdisk is composed of four circular arcs with different radii and thus an incident angle of a laser light parallel to the boundary is greater than the critical angle to be totally reflected. Also, the microdisk has an unidirectional emission characteristic due to a shape of the microdisk composed of four circular arcs. Accordingly, it is possible to implement a microdisk laser that has an ultra-high quality factor and unidirectionally emits light. Thus, it is possible to implement a sensor utilizing a high-quality factor microdisk laser that satisfies sensitivity and stability.

BEST MODE

Figure 1A:
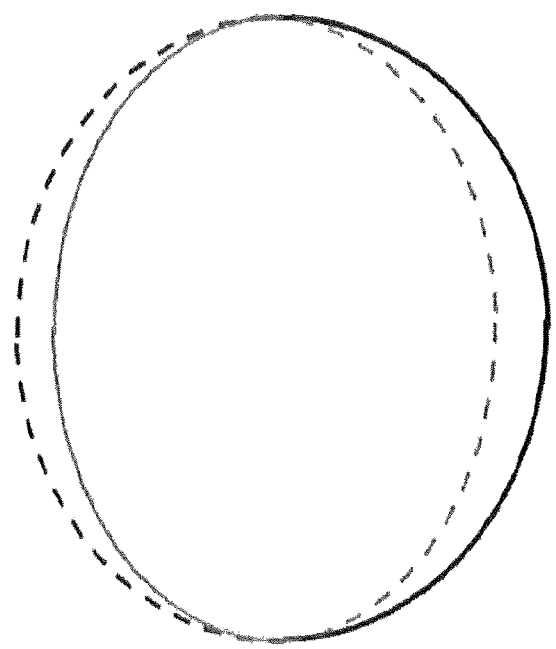
FIGS. 1A and 1B are diagrams associated with a unidirectionally emitting microdisk laser, which is a prototype of the present invention.

A microdisk according to an embodiment of the present invention is provided. The microdisk has a first arc having a first radius R1; third and fourth arcs tangentially connected to both ends of the first arc; and a second arc having a second radius R2 greater than the first radius R1 and tangentially connected to the third and fourth arcs.

An ultra-high quality factor resonance mode may be a resonance mode of the resonator formed in the form of a whispering gallery mode in a chaotic resonator.

The ultra-high quality factor resonance mode may be a resonance mode that is localized on a stable periodic orbit positioned at an edge of the chaotic resonator or an unstable periodic orbit positioned at an edge of the chaotic resonator.

The ultra-high quality factor resonance mode may be a resonance mode that is localized on a marginally unstable periodic orbit positioned at an edge of the chaotic resonator or an unstable periodic orbit positioned around the boundary of the chaotic resonator.

According to an embodiment, the microdisk may have emission intensity greater in one direction than in other directions. Preferably, the microdisk laser may unidirectionally emit light.

Also, when the third arc has a third radius R3 and the fourth arc has a fourth radius R4, the third radius and the fourth radius may be smaller than the first radius.

The first, second, third, and fourth arcs may each be formed as a circular arc or a portion of an ellipse.

According to an embodiment, the fourth radius R4 and the third radius R3 may be formed smaller than or equal to $1-10^{-7}$ times the first radius R1. Also, the fourth radius R4 and the third radius R3 may each be in the range between 5% and 99.99999% of the first radius R1.

According to an embodiment, the second radius R2 may be formed greater than or equal to $1+10^{-7}$ times the first radius R1. Also, the second radius R2 may be infinite so that the second arc becomes a straight line.

Points at which the first arc meets the third and fourth arcs and points at which the third and fourth arcs meet the second arc may each be a point at which the two corresponding arcs are tangentially connected to have the same first order derivative value.

Also, points at which the first arc meets the third and fourth arcs and points at which the third and fourth arcs meet the second arc may each be a point at which a difference in first order derivative value is 10% or less.

According to an embodiment, when the third arc has a third radius R3 and the fourth arc has a fourth radius R4, the third radius R3 may be equal to the fourth radius R4.

In order to achieve the described purpose, a microdisk laser according to another embodiment of the present invention is provided. The microdisk laser includes a power supply unit; a microdisk having a first arc having a first radius R1, third and fourth arcs tangentially connected to both ends of the first arc, and a second arc having a second radius R2 greater than the first radius R1 and tangentially connected to the third and fourth arcs; and an electrode formed by coating an upper surface of the microdisk with metal and configured to supply electric current.

According to an embodiment, in order to generate a whispering gallery mode, the microdisk may supply power along a path, where a whispering gallery mode is localized.

In order to achieve the described purpose, a microdisk laser according to still another embodiment of the present invention is provided. The microdisk laser includes a microdisk having a first arc having a first radius R1, third and fourth arcs tangentially connected to both ends of the first arc, and a second arc having a second radius R2 greater than the first radius R1 and tangentially connected to the third and fourth arcs; and a light supply unit configured to supply light to the microdisk to excite the microdisk.

According to an embodiment, in order to generate a whispering gallery mode, the light supply unit may supply light along an edge of the microdisk to excite the microdisk.

In order to achieve the described purpose, a microdisk according to still another embodiment of the present invention is provided. The microdisk is for emission with resonance having the form of a whispering gallery mode formed by total reflection, and the microdisk may have a first arc having a first radius R1, third and fourth arcs tangentially connected to both ends of the first arc, and a second arc tangentially connected to the third and fourth arcs.

MODE OF THE INVENTION

Hereinafter, the present invention will be described in detail with respect to the accompanying drawings and detailed embodiments. The following embodiments are used to describe the present invention in detail, and thus the scope of the present invention is not limited by the embodiments.

Figure 1B:
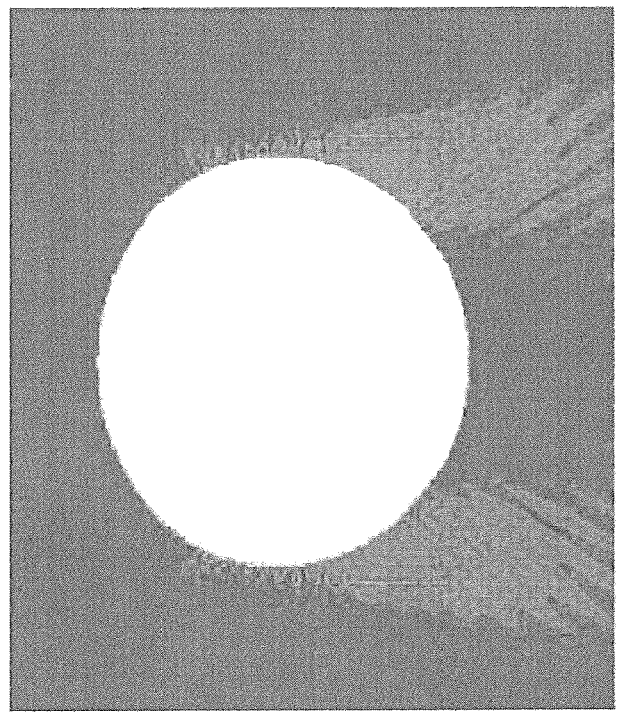

FIGS. 1A and 1B are diagrams associated with a unidirectionally emitting microdisk laser, which is a prototype of the present invention.

Referring to FIGS. 1A and 1B, a resonator having a half-circular and half-elliptic shape is shown. FIG. 1A shows a half-circular and half-elliptic shape of a laser, and FIG. 1B shows directionality of light when a resonance mode formed inside a resonator escapes from the resonator. As shown in FIGS. 1A and 1B, it can be seen that a laser having this shape emits light in one direction.

However, unidirectionally emitting microdisk lasers that have been developed up to now, including such a prototype, solve a problem with unidirectional emission, but have so low quality factors that the unidirectionally emitting microdisk lasers are difficult to commercialize for sensors.

Figure 2:
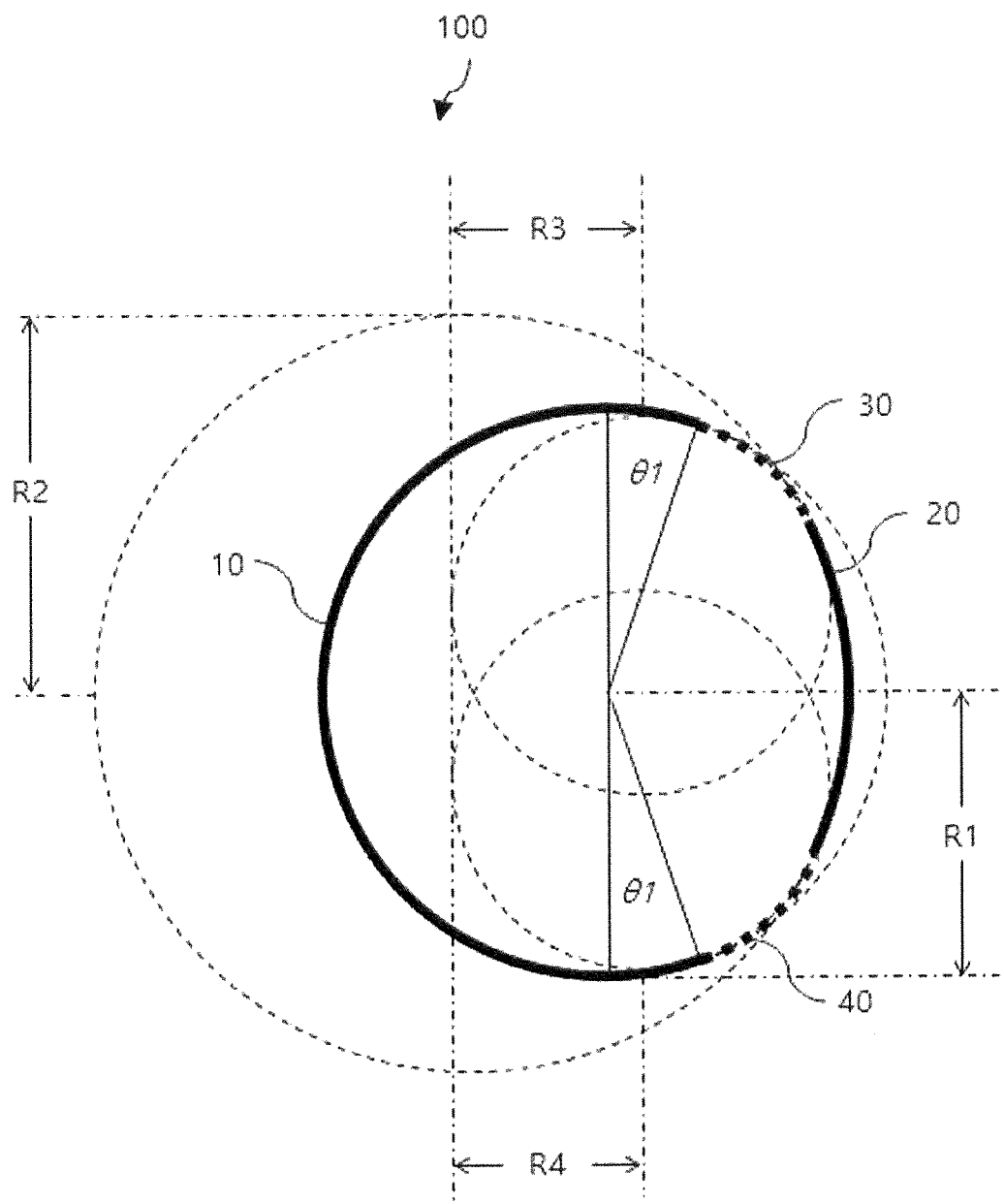
FIG. 2 is a conceptual diagram of a microdisk according to an embodiment of the present invention.

FIG. 2 is a conceptual diagram of a microdisk according to an embodiment of the present invention.

Referring to FIG. 2, a microdisk 100 according to an embodiment of the present invention has a first arc 10 having a first radius R1. A third arc 30 and a fourth arc 40, each of which has a radius smaller than the first radius R1, are connected to the first arc 10 inside a circle formed using the first arc 10. In this case, the first arc 10 and the second arc 30 have the same first order derivative value at the connection point, and the first arc 10 and the fourth arc 40 have the same first order derivative value at the connection point. A second arc 20 having a second radius R2 greater than the first radius R1 is connected to the third arc 30 and the fourth arc 40. Even in this case, the second arc 20 and the third arc 30 are designed to have the same first order derivative value at the connection point, and the second arc and the fourth arc are designed to have the same first order derivative value at the connection point. The third arc 30 and the fourth arc 40 are represented by dotted lines. This is just to describe a difference in curvature, and thus material or the like needs not to be different.

In this shape, the first arc 10 is connected to the third arc 30 and the fourth arc at the connection points, and the third arc 30 and the fourth arc 40 are connected to the second arc 20 at the connection points. In a shape formed by only such circles, light traveling inside a resonator is in a whispering gallery mode and thus is totally reflected. Accordingly, the light is not emitted to the outside, except evanescent waves. However, when light travels through circles having different curvatures, the light has an incidence angle that is gradually increasing. As a result, the light goes out. At this point, the light has unidirectionality.

In the microdisk, a third radius R3, which is the radius of the third arc 30, may be equal to a fourth radius R4, which is the radius of the fourth arc 40. Also, in this shape, the circle does not need to be a circular arc, but may be an ellipse. That is, a resonator having the same shape as that of the present invention may be formed by only ellipses or by a combination of ellipses and circles. Alternatively, the resonator may be formed by a combination of various curved figures having curved lines.

The shape of the microdisk according to the present invention was designed using the concept of quantum chaos. Characteristics of emission, i.e., unidirectional emission was confirmed by using a wave function obtained through a ray tracing method, a spatio-temporal differential equation, and a boundary element method. Thus, it is possible to obtain an optimal design for the microdisk laser according to the embodiment.

The quantum chaos is used as a method of finding modes generated in a small space and their characteristics, and the spatio-temporal differential equation is used as a tool for finding a pattern occurring in the natural world and its temporal variation. By analyzing modes of a laser emission in the microdisk by combining such characteristics and utilizing both the concepts of the quantum chaos and the spatio-temporal differential equation, it is possible to know in which shape the laser should be designed to have directionality.

When a micro laser is designed on the basis of the analysis methods, it is possible to know emission direction and characteristics of the designed microdisk laser.

Figure 3:
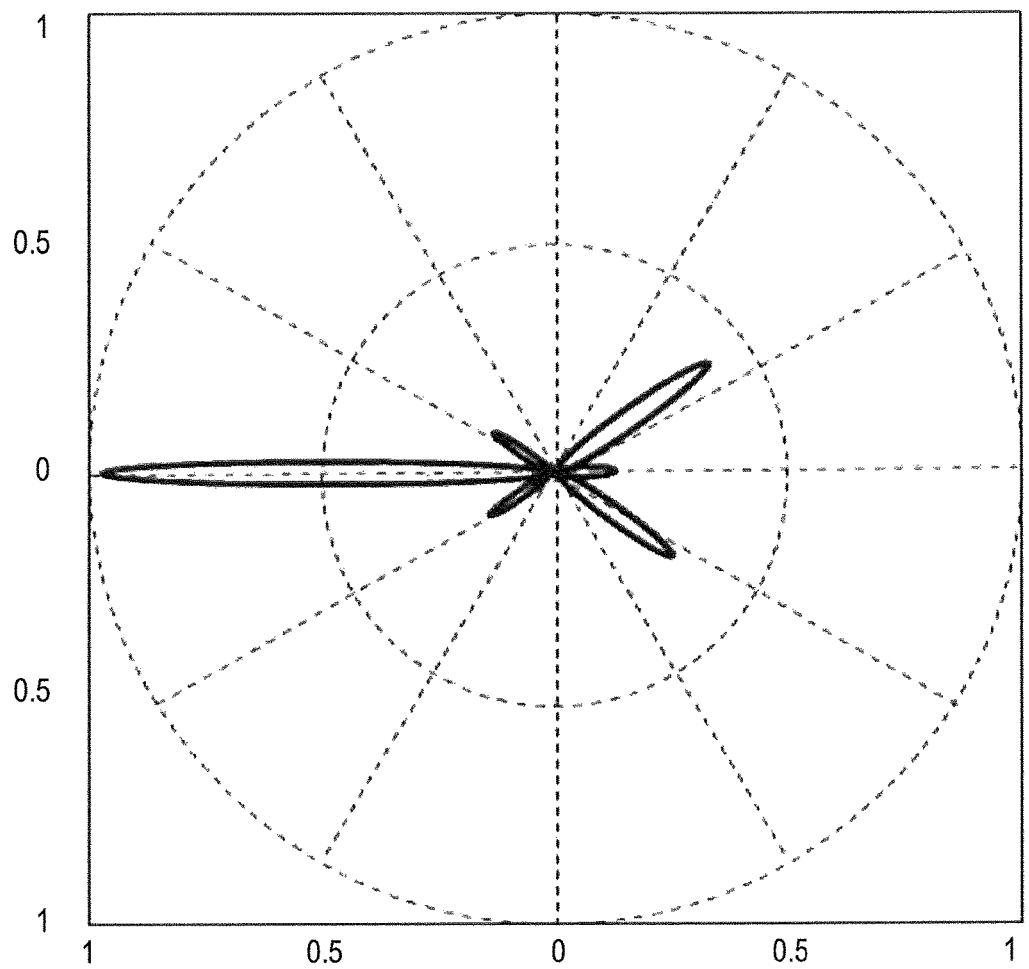
FIG. 3 shows emission direction of a microdisk laser, which is analyzed by a ray tracing method according to an embodiment of the present invention.

FIG. 3 shows emission direction of a microdisk laser, which is analyzed by a ray tracing method according to an embodiment of the present invention.

Referring to FIG. 3, the emission direction shown in the figure is a result of a light emission direction through a ray tracing method in microdisk designed according to an embodiment of the present invention.

Here, for the calculation, the first radius R1 of FIG. 2 is set to 1, the third radius R3 and the fourth radius R4 are each set to 0.999*R1, the second radius R2 is set to 1.0001*R1, and θ1 in FIG. 2 is set to zero degrees. The calculation is to find a direction in which the light escapes from the resonator after the light is reflected 100 times while a case in which light starts from any 1,000 points when the light travels in any 1,000 directions is set as initial values. As can be seen in FIG. 3, the light is emitted in one direction. This light was observed far distance from the microdisk boundary to check the directionality of the light corresponding to the angle. In detail, the intensity of light was observed depending on the angle at a point away from the center of the first arc 10 having the first radius R1 by a factor of 100 of the first radius R1.

According to this experiment, when the fourth radius R4 and the third radius R3 was equal to or smaller than $1-10^{-7}$ times the first radius R1, it could be found that unidirectional emission of light and a quality factor were obtained under an optimal condition. This range may be more widely interpreted as a range having the unidirectional emission of light and the quality factor capable of functioning as a sensor. When the fourth radius R4 and the third radius R3 be within the range between 5% and 99.99999% of the first radius R1, this is interpreted as the range capable of functioning as a sensor. In addition, an optimal sensor condition might be satisfied when the second radius R2 was greater than $1+10^{-7}$ times the first radius R1.

In particular, it is more advantageous that points at which the first arc meets the third and fourth arcs or points at which the third and fourth arcs meet the second arc be designed to have first order derivative values of zero. When the points are not designed to have first order derivative values of zero, it is more advantageous that the difference in first order derivative value at the points at which the first arc meets the third and fourth arcs and the points at which the third and fourth arcs meet the second arc be in the range of 10% or less.

When this range is more widely interpreted to have the unidirectional emission of light and the quality factor capable of functioning as a sensor, the difference in first order derivative value at the points at which the first arc meets the third and fourth arcs and the points at which the third and fourth arcs meet the second arc be in the range of 0% to 95%.

In order to find whether there was a laser emission mode in which such light was emitted, directionality of a wavefunction formed in the whispering gallery mode was observed in the resonator having the shape according to an embodiment of the present invention. This calculation is carried out to solve the wavefunction by using the boundary element method.

Figure 4A:
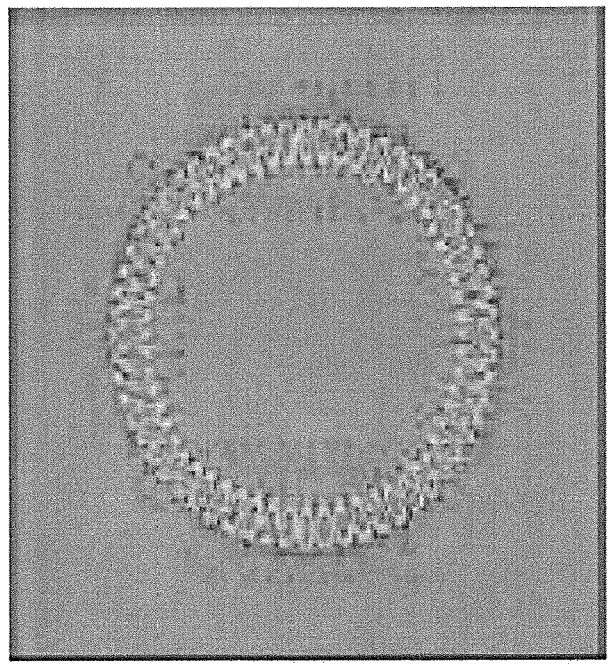
FIGS. 4A and 4B are diagrams showing unidirectional emission of a microdisk according to the embodiment.
Figure 4B:
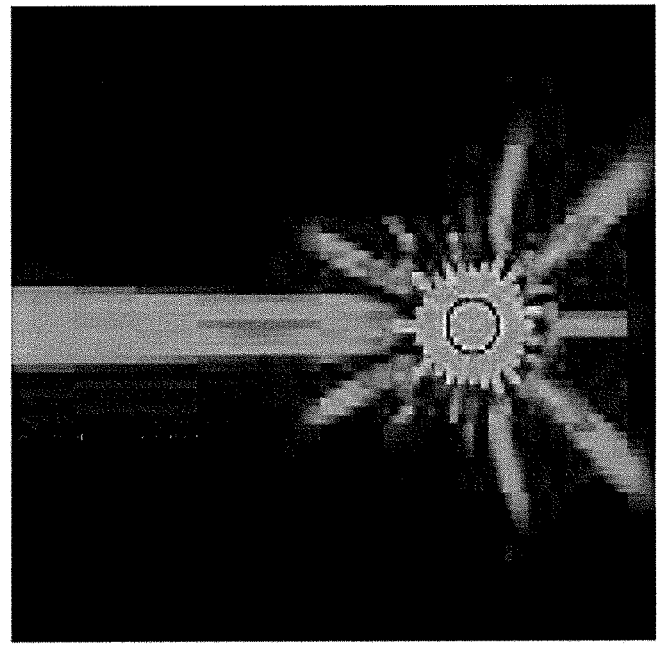

FIGS. 4A and 4B are diagrams showing unidirectional emission of a microdisk according to the embodiment.

FIG. 4A is a diagram showing a whispering gallery mode formed along a boundary of the microdisk according to an embodiment of the present invention. FIG. 4B shows a result of obtaining light intensity according to angles of the perimeter of the interface from a point distant by a factor of 100 of the first radius R1 of FIG. 2 in order to observe whether the whispering gallery mode emits light in one direction. As can be seen in FIG. 4, the whispering gallery mode emits light in one direction.

Quality factor of a resonance mode can be obtained from a complex eigenvalue given by the following Equation 1 when light escape from a resonator like a laser:

$$\lambda = a + ib.$$ Equation [1]

The quality factor is defined as Q=a/2b in a complex-number eigenvalue, and thus was solved by using the eigenvalue. When the solution is obtained through computer simulation, the boundary of the resonator looks a straight line if the number of meshes of the boundary is small and also looks a circle if the number of meshes is infinite. Accordingly, the quality factor of the resonance mode was found while increasing the number of meshes.

Figure 5:
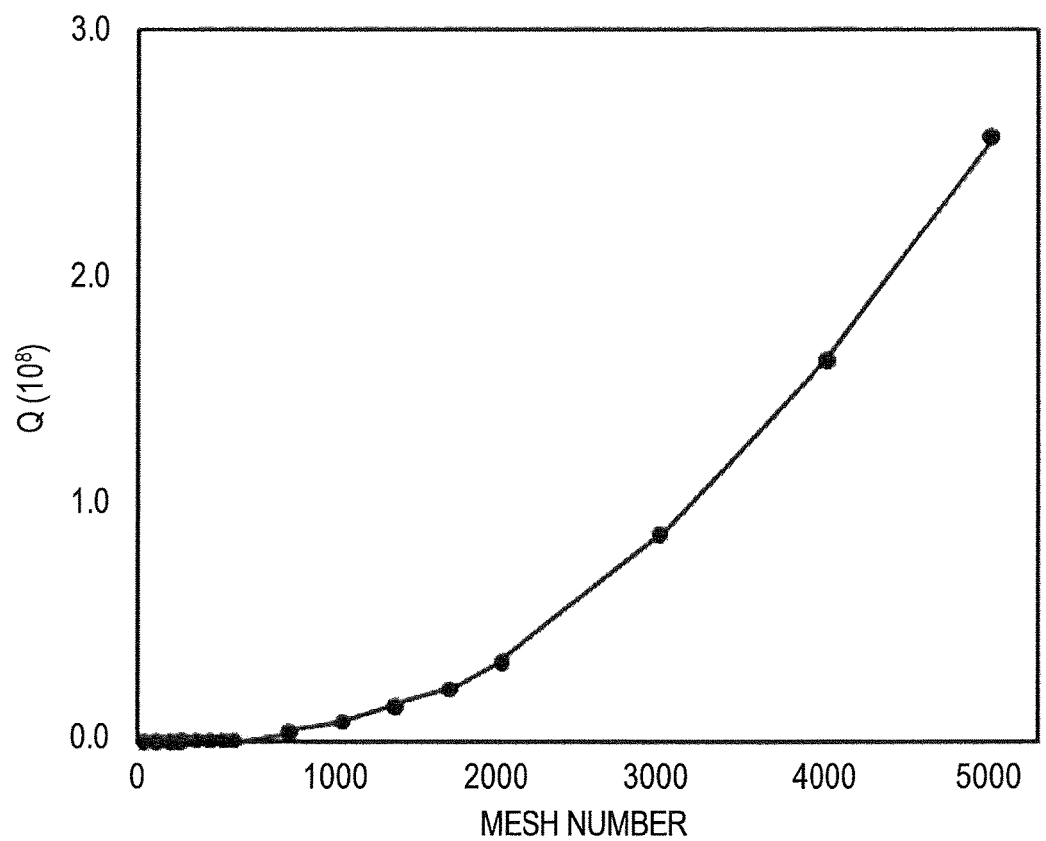
FIG. 5 is a graph showing a quality factor of a microdisk depending on the number of mesh according to an embodiment of the present invention.

FIG. 5 is a graph showing a quality factor of a microdisk depending on the number of mesh according to an embodiment of the present invention.

Referring to FIG. 5, the result of finding the quality factor of the microdisk according to the embodiment shows that the quality factor exceeds $2.6 \times 10^8$ when the number of meshes is 4,800. The quality factor was measured by means of the maximum performance of currently developed computers. Accordingly, it can be seen that when a laser is formed using the microdisk according to the embodiment, the laser emits light in one direction as shown in FIGS. 3, 4A, and 4B and has an ultra-high quality factor as shown in FIG. 5.

Figure 6:
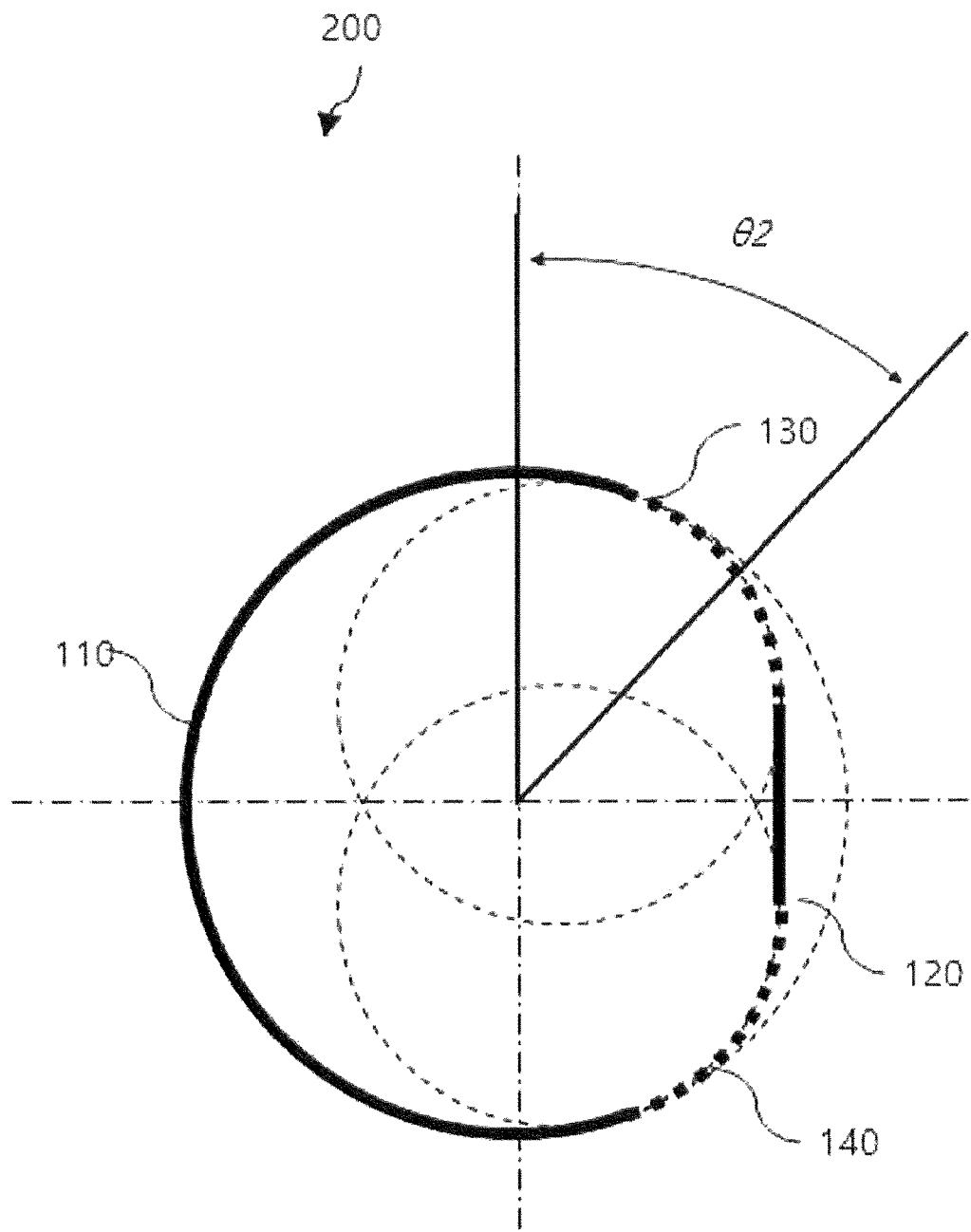
FIG. 6 is a diagram showing a shape of a microdisk to be compared with an embodiment of the present invention.
Figure 7A:
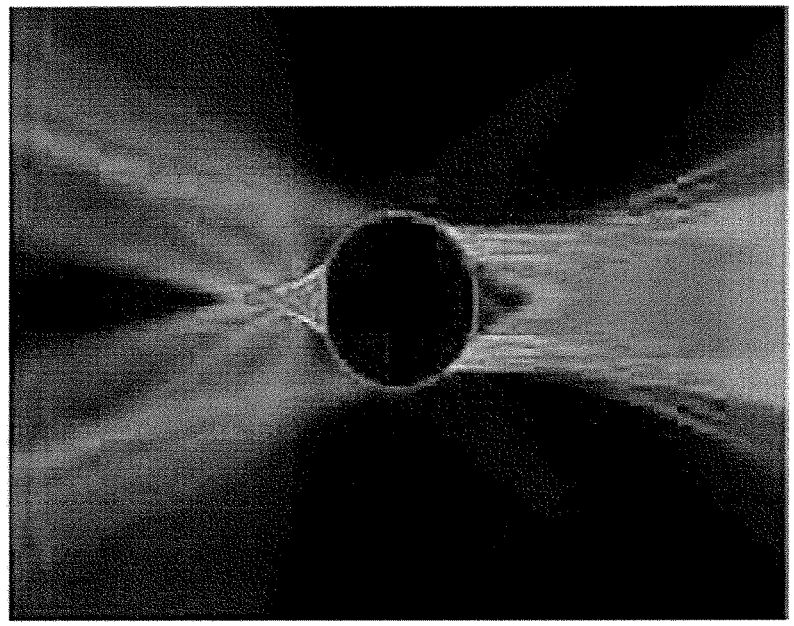
FIGS. 7A to 7C are diagrams showing directionality of light according to an angle of the microdisk of FIG. 6.
Figure 7B:
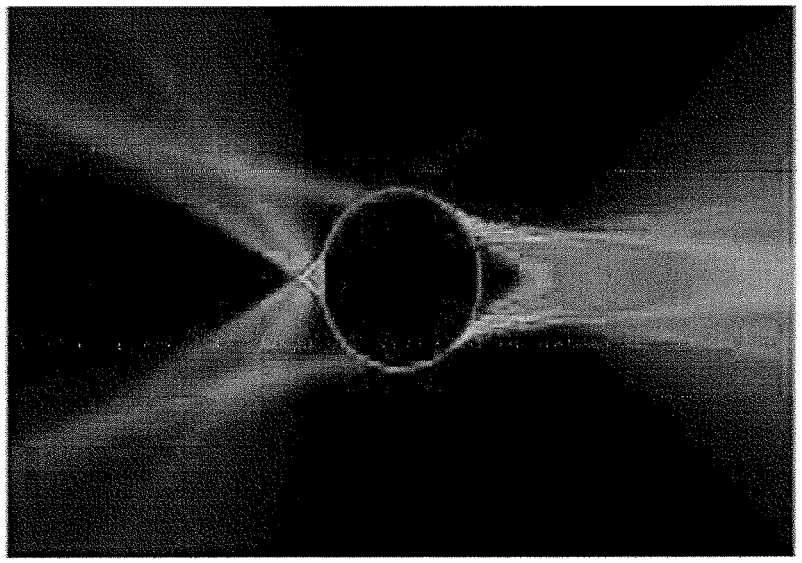
Figure 7C:
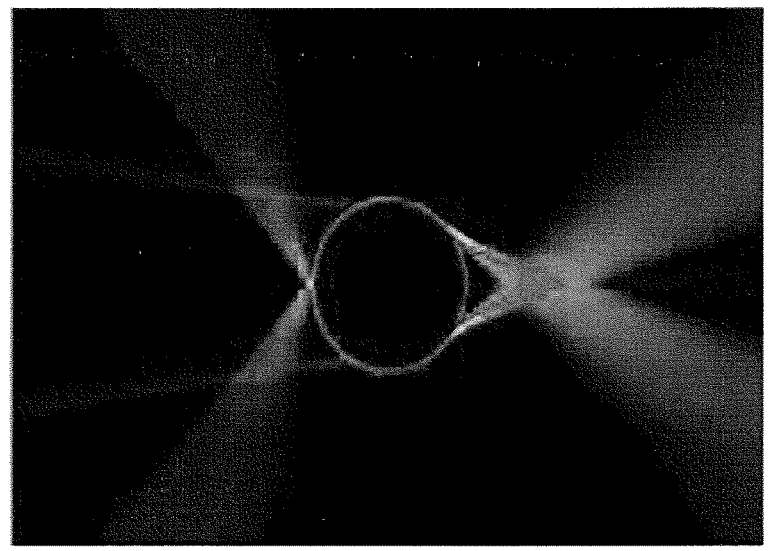

FIG. 6 is a diagram showing a shape of a microdisk to be compared with an embodiment of the present invention. FIGS. 7A to 7C are diagrams showing directionality of laser emission depending on an angle of the microdisk of FIG. 6.

Referring to FIG. 6, a microdisk 200 is substantially the same as the microdisk 100 of FIG. 2, except that a second arc 120 is an infinite radius. The microdisk 200 has a straight line when the radius of a large circular arc in a resonator is set to be infinite. As a result, the microdisk 200 has a shape composed of three circular arcs and one straight line. In this case, the directionality of light may be determined according to the position and size of a smaller circular arc. Even at this point, the light is emitted in one direction. FIG. 6 shows the directionality of light in a resonator when the radius of a largest circular arc is infinite. In this case, when the size of the smaller circular arc is set to 0.5*R1, the shape of the resonator is as shown in FIG. 6.

In this case, when the directionality of laser emission is observed depending on the angle, it can be seen that light escaping from two positions as shown in FIG. 7A emits in one direction when the angle θ1 is 60 degrees. When the angle increases to 70 degrees, it can be seen that the light is focused on one point as shown in FIG. 7B. When the angle of θ1 increases to 80 degrees, the focusing point is located closer thereto, as shown in FIG. 7C. The focusing of light in this way is more effective than focusing of light with a lens and thus may be conveniently used when the light is focused on an optical fiber or a waveguide.

Figure 8:
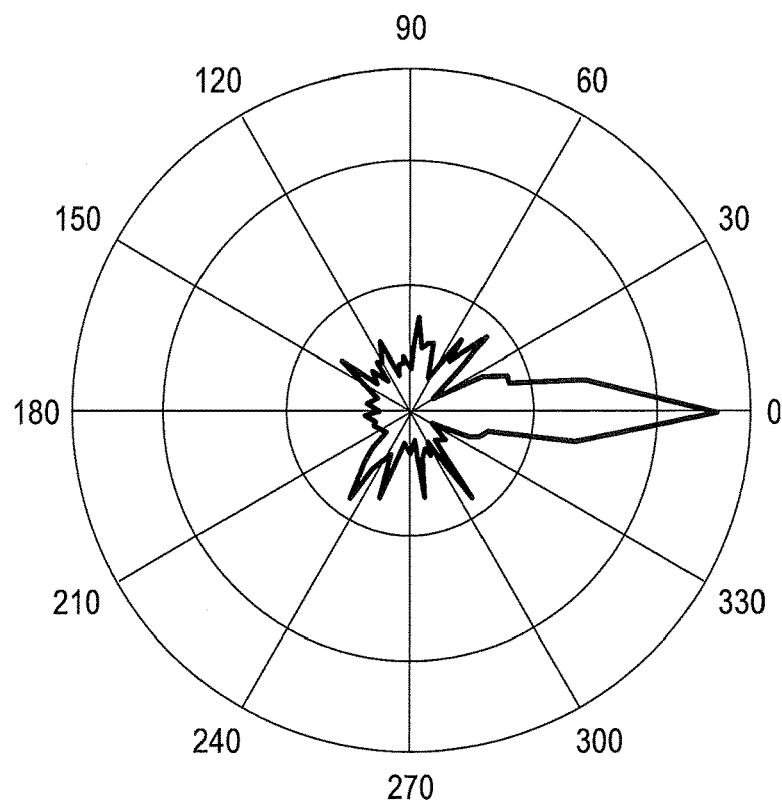
FIG. 8 shows the emission direction of a laser according to an embodiment of the present invention.

In order to confirm the emission direction of the laser, the radii of the third arc and the fourth arc were set to ½ of that of the first arc, and the radius of the second arc was set to be infinite so that the second arc might become a straight line. The angle θ1 of FIG. 2 was designed to be 60 degrees. Thus, the laser was fabricated with InGaAsP semiconductor having a refractive index of 3.3 and used in this experiment. FIG. 8 shows the emission direction of the laser fabricated in such a way, and it can be seen that the laser emits light in one direction like a theoretical value.

In order to achieve the described purpose, a configuration of a microdisk according to still another embodiment of the present invention is provided. The microdisk is for generation of a resonance having the form of a whispering gallery mode formed by total reflection, and the microdisk may have a first arc having a first radius R1, third and fourth arcs tangentially connected to both ends of the first arc, and a second arc connected to the third and fourth arcs.

As described above, preferred embodiments of the present invention have been described in detail. However, it will be appreciated by those skilled in the art that various modifications may be made therein without departing from the spirit and scope of the present invention as defined in the accompanying claims.

In particular, for example, in a resonator having such a shape, the positions of small circular arcs change depending on the sizes thereof in order to satisfy a condition for generation in one direction. Light may be emitted in one direction when the angle θ1 of FIG. 2 is zero degrees as shown in FIG. 3 or when the angle θ1 of FIG. 2 is 60 degrees as shown in FIG. 7. Alternatively, the positions of small circular arcs change depending on conditions for focusing light. Also, as shown in FIG. 2, the size of a smaller circular arc was set to 99.9% of the radius of the central circle, and the size of a larger circular arc was set to 100.1% of the radius of the central circle. Even under the condition, it was shown that the micro resonator laser emitted light in one direction. Therefore, the size of the smaller circular arc may be just slightly smaller than the size of the central circle, and the radius of the larger circular arc may be just slightly larger than the radius of the central circle. Accordingly, modifications of the embodiments of the present invention cannot depart from the scope of the present invention.

As described above, the present invention proposes a microdisk laser designed to have a boundary of a resonator composed of four circular arcs and having characteristics of unidirectional emission in which total reflection occurs because light traveling therein has an incidence angle greater than a the critical angle and also in which light is unidirectionally emitted due to four circular arcs having different radii.

The invention claimed is:

1. A microdisk for forming a high quality factor resonance mode in a chaotic resonator, the microdisk comprising:
a first arc having a first radius R1;
third and fourth arcs directly and tangentially connected to both ends of the first arc; and
a second arc having a second radius R2 greater than the first radius R1 and tangentially connected to the third and fourth arcs,
wherein the first, second, third, and fourth arcs are each a circular arc,
wherein when the third arc has a third radius R3 and the fourth arc has a fourth radius R4, the third radius and the fourth radius are smaller than the first radius.

2. The microdisk of claim 1, wherein the high quality factor resonance mode is a resonance mode of the resonator formed in the form of a whispering gallery mode in the chaotic resonator.

3. The microdisk of claim 1, wherein the high quality factor resonance mode is a resonance mode that is localized on a stable periodic orbit positioned at an edge of the chaotic resonator or an unstable periodic orbit positioned at an edge of the chaotic resonator.

4. The microdisk of claim 1, wherein the high quality factor resonance mode is a resonance mode that is localized on a marginally unstable periodic orbit positioned at an edge of the chaotic resonator or an unstable periodic orbit positioned around the boundary of the chaotic resonator.

5. The microdisk of claim 1, wherein emission intensity is greater in one direction than in other directions.

6. The microdisk of claim 1, wherein the fourth radius R4 and the third radius R3 are smaller than or equal to $1-10^{-7}$ times the first radius R1.

7. The microdisk of claim 1, wherein the fourth radius R4 and the third radius R3 each be in the range between 5% and 99.99999% of the first radius R1.

8. The microdisk of claim 1, wherein the second radius R2 is greater than or equal to $1+10^{-7}$ times the first radius R1.

9. The microdisk of claim 1, wherein the second radius R2 is infinite so that the second arc becomes a straight line.

10. The microdisk of claim 1, wherein points at which the first arc meets the third and fourth arcs and points at which the third and fourth arcs meet the second arc are each a point at which the two corresponding arcs are tangentially connected to have the same first order derivative value.

11. The microdisk of claim 1, wherein points at which the first arc meets the third and fourth arcs and points at which the third and fourth arcs meet the second arc are each a point having a difference in first order derivative value of 10% or less.

12. The microdisk of claim 1, wherein when the third arc has a third radius R3 and the fourth arc has a fourth radius R4, the third radius R3 is equal to the fourth radius R4.

13. The microdisk of claim 1, wherein the first, second, third, and fourth arcs are each a circular arc having a finite radius.

14. A microdisk laser comprising:
a power supply unit;
a microdisk having a first arc having a first radius R1, third and fourth arcs directly and tangentially connected to both ends of the first arc, and a second arc having a second radius R2 greater than the first radius R1 and tangentially connected to the third and fourth arcs; and
an electrode formed by coating an upper surface of the microdisk with metal and configured to supply electric current,
wherein the first, second, third, and fourth arcs are each a circular arc,
wherein when the third arc has a third radius R3 and the fourth arc has a fourth radius R4, the third radius and the fourth radius are smaller than the first radius.

15. The microdisk laser of claim 14, wherein the microdisk supplies power along a path, wherein a whispering gallery mode is localized for unidirectional emission of the whispering gallery mode.

16. A microdisk laser comprising:
a microdisk having a first arc having a first radius R1, third and fourth arcs directly and tangentially connected to both ends of the first arc, and a second arc having a second radius R2 greater than the first radius R1 and tangentially connected to the third and fourth arcs; and
a light supply unit configured to supply light to the microdisk to excite the microdisk,
wherein the second radius R2 is infinite so that the second arc becomes a straight line,
wherein when the third arc has a third radius R3 and the fourth arc has a fourth radius R4, the third radius and the fourth radius are smaller than the first radius.

* * * * *